(12) United States Patent
Lareau et al.

(10) Patent No.: US 10,319,466 B2
(45) Date of Patent: Jun. 11, 2019

(54) INTELLIGENT FILTERING OF HEALTH-RELATED INFORMATION

(71) Applicant: Medicomp Systems, Inc., Chantilly, VA (US)

(72) Inventors: David P. Lareau, Oakton, VA (US); Luke Andrew Stratman, Ashburn, VA (US)

(73) Assignee: MEDICOMP SYSTEMS, INC, Chantilly, VA (US)

( * ) Notice: Subject to any disclaimer, the term of this patent is extended or adjusted under 35 U.S.C. 154(b) by 0 days.

(21) Appl. No.: 13/772,093

(22) Filed: Feb. 20, 2013

(65) Prior Publication Data

US 2013/0231957 A1 Sep. 5, 2013

Related U.S. Application Data

(60) Provisional application No. 61/600,927, filed on Feb. 20, 2012.

(51) Int. Cl.
*G16H 10/60* (2018.01)

(52) U.S. Cl.
CPC .................. *G16H 10/60* (2018.01)

(58) Field of Classification Search
CPC ...... G06Q 50/22; G06Q 50/24; G06F 19/322; G06F 19/323–19/327; G06F 19/00; G06F 19/30; G06F 19/34; G06F 19/36; G16H 10/00; G16H 10/60; G16H 15/00; G16H 50/00; G16H 50/70
USPC ....................................................... 705/2, 3
See application file for complete search history.

(56) References Cited

U.S. PATENT DOCUMENTS

| | | | | |
|---|---|---|---|---|
| 7,610,192 | B1* | 10/2009 | Jamieson | G06Q 50/22 704/1 |
| 2005/0027564 | A1* | 2/2005 | Yantis | G06F 17/30569 705/2 |
| 2005/0027566 | A1* | 2/2005 | Haskell | G06F 17/2735 705/2 |
| 2005/0107672 | A1* | 5/2005 | Lipscher | G06F 19/3456 600/300 |
| 2005/0108054 | A1* | 5/2005 | Gottlieb | G06K 9/723 705/2 |
| 2006/0031218 | A1* | 2/2006 | Cipollone | G06F 17/30675 |
| 2006/0122865 | A1* | 6/2006 | Preiss | G06Q 10/0633 705/2 |
| 2006/0253431 | A1* | 11/2006 | Bobick | G06F 17/2795 |
| 2007/0088559 | A1* | 4/2007 | Kim | G06F 19/3418 715/705 |
| 2007/0244911 | A1* | 10/2007 | Dick | G06F 17/2247 |
| 2008/0016042 | A1* | 1/2008 | McKnight | G06Q 10/087 |
| 2008/0021288 | A1* | 1/2008 | Bowman | G06F 19/3443 600/300 |
| 2008/0046292 | A1* | 2/2008 | Myers | G06F 17/30557 705/3 |

(Continued)

*Primary Examiner* — Jason S Tiedeman
(74) *Attorney, Agent, or Firm* — Buchanan Ingersoll & Rooney PC

(57) ABSTRACT

Intelligent filtering of health-related information includes receiving health-related information including items encoded in one or more external standard terminologies. The health-related information is converted from the external standard terminologies into an internal medical terminology. Items within the health-related information are then identified that are related to a selected term of the internal medical terminology.

20 Claims, 11 Drawing Sheets

| ITEMS FROM ENCOUNTER NOTE FOR ASTHMA | | | |
|---|---|---|---|
| SCT:49727002:COUGH | | | |
| SCT:272040008:REPORTED WHEEZING | | | |
| ICD9:493.9:ASTHMA | | | |
| LOINC:81146:CBC WITH DIFFERENTIAL | | | |

TERMINOLOGY MAPPING TABLE FOR ASTHMA (CODE 328881)

| EXTERNAL STANDARD TERMINOLOGY | RELATIONSHIP | CODE | DESCRIPTION |
|---|---|---|---|
| ICD-9-CM | | 493 | ASTHMA |
| ICD-9-CM | 342 | 493. | ASTHMA, UNSPECIFIED |
| ICD-9-CM | | 493.9 | ASTHMA, UNSPECIFIED, UNSPECIFIED |
| ICD-9-CM | | V17.5 | FAMILY HISTORY OF CERTAIN CHRONIC DISABLING DISEASES, ASTHMA |
| ICD-10-CM | SAME AS | J45.90 | UNSPECIFIED ASTHMA |
| ICD-10-CM | SAME AS | J45.909 | UNSPECIFIED ASTHMA, UNCOMPLICATED |
| ICD-10-CM | BROADER THAN | J45.998 | OTHER ASTHMA |
| ICD-10-CM | NARROWER THAN | Z82.5 | FAMILY HISTORY OF ASTHMA AND OTHER CHRONIC LOWER RESPIRATORY DISEASES |
| SNOMED-CT | SAME AS | 160377001 | FAMILY HISTORY: ASTHMA (SITUATION) |
| SNOMED-CT | SAME AS | 195967001 | ASTHMA (DISORDER) |
| SNOMED-CT | BROADER THAN | 195977004 | MIXED ASTHMA (DISORDER) |
| SNOMED-CT | BROADER THAN | 225057002 | BRITTLE ASTHMA (DISORDER) |
| SNOMED-CT | BROADER THAN | 233679003 | LATE ONSET ASTHMA (DISORDER) |
| SNOMED-CT | BROADER THAN | 233683003 | HAY FEVER WITH ASTHMA (DISORDER) |
| SNOMED-CT | BROADER THAN | 233686006 | ASPIRIN-SENSITIVE ASTHMA WITH NASAL POLYPS (DISORDER) |
| SNOMED-CT | BROADER THAN | 233688007 | SULFITE-INDUCED ASTHMA (DISORDER) |
| SNOMED-CT | BROADER THAN | 266364000 | ASTHMA ATTACK (DISORDER) |
| SNOMED-CT | BROADER THAN | 30352005 | ALLERGIC-INFECTIVE ASTHMA (DISORDER) |
| SNOMED-CT | BROADER THAN | 304527002 | ACUTE ASTHMA (DISORDER) |
| SNOMED-CT | BROADER THAN | 370218001 | MILD ASTHMA (DISORDER) |
| SNOMED-CT | BROADER THAN | 370219009 | MODERATE ASTHMA (DISORDER) |
| SNOMED-CT | BROADER THAN | 370220003 | OCCASIONAL ASTHMA (DISORDER) |

(56) References Cited

U.S. PATENT DOCUMENTS

| | | | | |
|---|---|---|---|---|
| 2008/0091464 A1* | 4/2008 | Lipscher | G06Q 50/22 | 705/2 |
| 2008/0215367 A1* | 9/2008 | Marshall | G06F 19/322 | 705/3 |
| 2008/0216010 A1* | 9/2008 | Lareau | G06F 17/2247 | 715/783 |
| 2009/0055378 A1* | 2/2009 | Alecu | G06F 17/30616 | |
| 2009/0210450 A1* | 8/2009 | Goltra | G06F 19/325 | |
| 2010/0017222 A1* | 1/2010 | Yeluri | G06F 19/327 | 705/2 |
| 2010/0131299 A1* | 5/2010 | Hasan | G06F 19/324 | 705/3 |
| 2010/0161354 A1* | 6/2010 | Lim | G06F 19/3418 | 705/3 |
| 2010/0179827 A1* | 7/2010 | McCallie, Jr. | G06F 17/30657 | 705/3 |
| 2010/0274584 A1* | 10/2010 | Kim | G06Q 50/24 | 705/3 |
| 2010/0318549 A1* | 12/2010 | Mayr | G16H 10/60 | 707/759 |
| 2011/0004628 A1* | 1/2011 | Armstrong | G06F 17/30672 | 707/778 |
| 2012/0060216 A1* | 3/2012 | Chaudhri | G06Q 50/22 | 726/21 |
| 2012/0110016 A1* | 5/2012 | Phillips | G06F 17/30598 | 707/780 |
| 2012/0215559 A1* | 8/2012 | Flanagan | G06Q 10/10 | 705/3 |
| 2012/0239671 A1* | 9/2012 | Chaudhri | G06Q 10/06 | 707/756 |
| 2012/0290322 A1* | 11/2012 | Bergman | G06Q 50/24 | 705/3 |
| 2013/0006653 A1* | 1/2013 | Mills | G06Q 10/10 | 705/2 |
| 2013/0046529 A1* | 2/2013 | Grain | G06F 17/289 | 704/2 |
| 2013/0046758 A1* | 2/2013 | Kim | G06F 17/30737 | 707/723 |
| 2013/0054678 A1* | 2/2013 | Williams | G06F 17/243 | 709/203 |
| 2014/0006013 A1* | 1/2014 | Markatou | G06F 17/3061 | 704/9 |

* cited by examiner

ITEMS FROM ENCOUNTER NOTE FOR ASTHMA — 282 / 138
SCT:49727002:COUGH — 292
SCT:27204008:REPORTED WHEEZING — 294
ICD9:493.9:ASTHMA — 296 / 248
LOINC:81146:CBC WITH DIFFERENTIAL — 298
TERMINOLOGY MAPPING TABLE FOR ASTHMA (CODE 328881) — 264

| EXTERNAL STANDARD TERMINOLOGY | RELATIONSHIP | CODE | DESCRIPTION |
|---|---|---|---|
| ICD-9-CM | | 493 | ASTHMA |
| ICD-9-CM | | 493 (342) | ASTHMA, UNSPECIFIED |
| ICD-9-CM | | 493.9 | ASTHMA, UNSPECIFIED, UNSPECIFIED |
| ICD-9-CM | | V17.5 | FAMILY HISTORY OF CERTAIN CHRONIC DISABLING DISEASES, ASTHMA |
| ICD-10-CM | SAME AS | J45.90 | UNSPECIFIED ASTHMA |
| ICD-10-CM | SAME AS | J45.909 | UNSPECIFIED ASTHMA, UNCOMPLICATED |
| ICD-10-CM | BROADER THAN | J45.998 | OTHER ASTHMA |
| ICD-10-CM | NARROWER THAN | Z82.5 | FAMILY HISTORY OF ASTHMA AND OTHER CHRONIC LOWER RESPIRATORY DISEASES |
| SNOMED-CT | SAME AS | 160377001 | FAMILY HISTORY: ASTHMA (SITUATION) |
| SNOMED-CT | SAME AS | 195967001 | ASTHMA (DISORDER) |
| SNOMED-CT | BROADER THAN | 195977004 | MIXED ASTHMA (DISORDER) |
| SNOMED-CT | BROADER THAN | 225057002 | BRITTLE ASTHMA (DISORDER) |
| SNOMED-CT | BROADER THAN | 233679003 | LATE ONSET ASTHMA (DISORDER) |
| SNOMED-CT | BROADER THAN | 233683003 | HAY FEVER WITH ASTHMA (DISORDER) |
| SNOMED-CT | BROADER THAN | 233686006 | ASPIRIN-SENSITIVE ASTHMA WITH NASAL POLYPS (DISORDER) |
| SNOMED-CT | BROADER THAN | 233688007 | SULFITE-INDUCED ASTHMA (DISORDER) |
| SNOMED-CT | BROADER THAN | 266364000 | ASTHMA ATTACK (DISORDER) |
| SNOMED-CT | BROADER THAN | 30352005 | ALLERGIC-INFECTIVE ASTHMA (DISORDER) |
| SNOMED-CT | BROADER THAN | 304527002 | ACUTE ASTHMA (DISORDER) |
| SNOMED-CT | BROADER THAN | 370218001 | MILD ASTHMA (DISORDER) |
| SNOMED-CT | BROADER THAN | 370219009 | MODERATE ASTHMA (DISORDER) |
| SNOMED-CT | BROADER THAN | 370220003 | OCCASIONAL ASTHMA (DISORDER) |

ITEMS FROM ENCOUNTER NOTE FOR ASTHMA
IMC:247:COUGH
IMC:273:REPORTED WHEEZING
IMC:328881:ASTHMA ⸺ 296'
IMC:81146:CBC WITH DIFFERENTIAL

364

ITEMS FROM PRESCRIPTION REFILLS
IMC:41470:ALBUTEROL
IMC:42681:CAPTOPRIL

366

ITEMS FROM ENCOUNTER NOTE FOR CARDIOLOGY
IMC:353:DIFFICULTY BREATHING ⸺ 306'
IMC:7156:ACCENTUATED P2 HEART SOUND
IMC:14634:2-D ECHOCARDIOGRAPHY
IMC:33268:CONGESTIVE HEART FAILURE
IMC:40075:OXYGEN
IMC:40595:DIGOXIN
IMC:40851:EDEMA

368

ITEMS FROM DISCHARGE SUMMARY
IMC:17212:SPUTUM BACTERIAL CULTURE
IMC:31527:BACTERIAL PNEUMONIA
IMC:40075:OXYGEN
IMC:40271:AMOXICILLIN
IMC:81146:CBC WITH DIFFERENTIAL

FIG. 8

| 32881 | ASTHMA | | COUNT = 281 |
|---|---|---|---|

| DESCRIPTION | IPR | |
|---|---|---|
| DIFFICULTY BREATHING | 1 | |
| RECENT DIFFICULTY BREATHING RAPIDLY PROGRESSIVE | 2 | |
| CHRONIC DIFFICULTY BREATHING | | |
| RECURRENT EPISODES OF ACUTE DIFFICULTY BREATHING | 1 | |
| DIFFICULTY BREATHING DURING EXERTION | 2 | |
| AWAKENING AT NIGHT SHORT OF BREATH | 1 | |
| COUGH | 1 | |
| DRY COUGH | | |
| CHRONIC COUGH | | |
| PERIODIC COUGHING | 2 | |
| COUGH ONLY WITH EXERTION | | |
| COUGH CAUSES AWAKENING FROM SLEEP | 2 | |
| COUGHING UP SPUTUM | | |
| COUGHING UP SPUTUM BLOOD-STREAKED | | |
| COUGHING UP SPUTUM WATERY | | |
| COUGHING UP SPUTUM MUCOID | | |
| COUGHING UP SPUTUM CLEAR | | |
| COUGHING UP SPUTUM WHITE | | |
| COUGHING UP SPUTUM IN LARGE AMOUNTS [....CUPS PER DA. | | |
| COUGHING UP BLOOD [HEMOPTYSIS] | 2 | |
| WHEEZING [AS A SYMPTOM] | 1 | |
| WHEEZING WORSE AT NIGHT | | |
| WHEEZING IS WORSE WITH COLD | | |
| WHEEZING WORSE DURING COLD WEATHER | | |
| WHEEZING RELATED TO BODY POSITION | | |
| WHEEZING OCCURS ONLY WITH EXERCISE | | |
| WHEEZING RECURS FROM TIME TO TIME [PERIODIC] | | |
| WHEEZING RECURS INTERMITTENTLY [EPISODIC] | 1 | |
| ANXIETY | | |
| ANXIETY WITH DIFFICULTY BREATHING | | |
| ANXIETY WITH CHEST PAIN OR DISCOMFORT | | |
| ANXIETY WITH CHOCKING OR SMOTHERING SENSATIONS | | |
| PREVIOUS HOSPITALIZATION FOR A PULMONARY PROBLEM | 1 | |
| PREVIOUS EMERGENCY ROOM VISIT FOR PULMONARY PROBLEM | 1 | |
| REPORTED PREVIOUS PULMONARY DISEASE | | |

FIG. 9

INTELLIGENT FILTERING OF HEALTH-RELATED INFORMATION

REFERENCE TO COPENDING APPLICATIONS

This application claims priority to U.S. Provisional Application 61/600,927, filed on Feb. 20, 2012 and entitled INTELLIGENT FILTERING OF HEALTH-RELATED INFORMATION, the entire disclosure of which is hereby incorporated by reference.

BACKGROUND

Health information exchanges are being established to promote the electronic exchange of health-related information between health care providers, which will require the participating health care providers to be able to transmit their data according to certain data standards. Examples of such data standards include the Systematized Nomenclature of Medicine—Clinical Terms (SNOMED CT) standard for diagnostic and clinical data, the Logical Observation Identifiers Names and Codes (LOINC) standard for laboratory data, the RxNorm standard for prescription drugs, and the International Statistical Classification of Diseases and Related Health Problems (ICD-9 and ICD-10) standards for billing and other purposes. Thus, a single healthcare provider may need to be able to send and receive data according to eight or nine different data standards. The data is then received by the health information exchange from the various health care providers, where it is stored and made available to other health care providers.

As a result of such initiatives, the medical community is quickly becoming overloaded with data. But, the data may contain vital information about a patient that the caregiver needs to know when treating that patient. For example, buried within the data may be information about the patient's current prescription drugs or preexisting conditions. It is important that relevant data be located and made available to the caregiver when it is needed so that appropriate treatment decisions can be made.

SUMMARY

In general terms, this disclosure is directed to intelligent filtering of health-related information.

One aspect is a method of filtering health-related information. The method includes receiving health-related information including items encoded in one or more external standard terminologies; converting the health-related information into converted health-related information including items encoded in an internal medical terminology; identifying one or more terms in the internal medical terminology related to a selected term of the internal medical terminology; and identifying items in the converted health-related information that match one or more of the terms related to the selected term Another aspect is an intelligent filtering system. The system includes at least one computing device including at least one processing device; and at least one computer readable storage device comprising data instructions, which when executed by the computing device cause the at least one computing device to generate: a data extraction engine that extracts items from health-related information in a native terminology; a terminology conversion engine that converts the items from the native terminology into an internal medical terminology to generate converted health-related information; a relevancy search engine that identifies items within the converted health-related information that are related to a selected term; and a user interface engine that presents the items that are related to the selected term to a caregiver.

BRIEF DESCRIPTION OF THE DRAWINGS

FIG. 6 is a schematic diagram illustrating the conversion of items from the health-related information to an internal medical terminology.

FIG. 8 is a schematic diagram illustrating the health-related information after conversion to the internal medical terminology.

FIG. 9 is a schematic diagram illustrating the identification of items from the health-related information that relate to a selected term.

DETAILED DESCRIPTION

Figure 1:
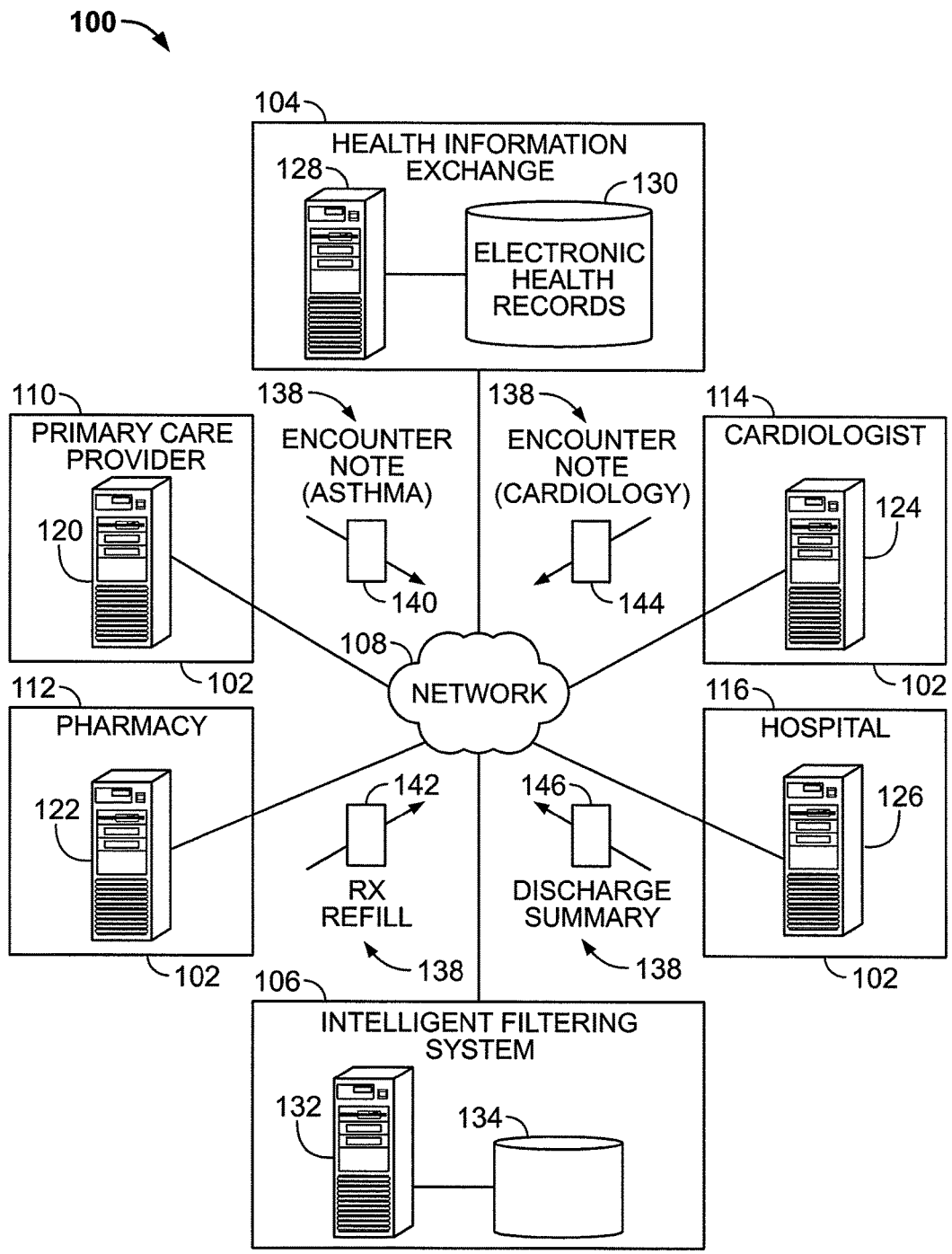
FIG. 1 is a schematic block diagram illustrating an exemplary healthcare information exchange network.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is schematic block diagram illustrating an exemplary healthcare information exchange network 100. The healthcare information exchange network 100 includes many different healthcare providers 102, a health information exchange system 104, and an intelligent filtering system 106.

The healthcare information exchange network 100 permits the exchange of healthcare-related information among multiple healthcare providers 102. In some embodiments, the healthcare information exchange network 100 includes one or more health information exchange system 104, but other embodiments do not include a health information exchange system 104. For example, data can be passed directly between the healthcare providers 102 (or through other third parties), rather than, or in addition to the interaction with the health information exchange system 104.

To illustrate the different healthcare providers that can participate, the exemplary healthcare information exchange network 100 includes healthcare providers such as a primary care provider 110, a pharmacy 112, a cardiologist 114, and a hospital 116. Although certain exemplary healthcare providers are explicitly identified herein, the healthcare exchange network also can include healthcare providers in addition to or in place of a primary care provider 110, a pharmacy 112, a cardiologist 114, and a hospital 116.

Typically, each healthcare provider 102 has at least one computing device, and oftentimes each healthcare provider has its own local area network with many computing devices, including one or more server computing devices and client computing devices. Caregivers at the healthcare providers 102 often interact with the client computing devices, or other terminal devices, which in turn communicate with the server computing devices. The server computing devices can communicate with another data communication network, such as the Internet, a local area network, or other data communication network, in which data can be communicated with the other healthcare providers 102 or with the health information exchange system 104.

The one or more possible computing devices at each of the healthcare providers 102 are represented by the computing devices 120, 122, 124, and 126, shown in FIG. 1. Further, there may be additional intermediary computing devices (such as those operated by third party services, such as medical records services, coding services, and the like) that participate in the data communications within the healthcare information exchange network 100, in at least some possible embodiments.

The health information exchange system 104 also includes one or more computing devices 128, and one or more data storage devices 130. The computing device 128 interacts with the healthcare provider computing devices 120, 122, 124, and 126 to send or receive data. Data received from the healthcare providers 102 is stored in the one or more data storage devices 130, as electronic health records. The electronic health records are associated with patients to which the records relate, and contain health-related information.

In a possible example, the healthcare providers 102 send health-related information 138 to the health-information exchange, or to each other, across the network 108, as shown in FIG. 1. The primary care provider 110 provides an encounter note 140 describing the primary care provider's 110 encounter with a patient relating to the patient's asthma. The pharmacy 112 provides a prescription refill 142 describing a prescription that is currently prescribed to the patient. The cardiologist 114 provides an encounter note describing the cardiologist's 114 encounter with the patient relating to cardiology. The hospital provides a discharge summary 146 describing the patient's recent hospital visit.

The various health-related information 138 communicated from the healthcare providers is typically encoded using one or more of multiple different standard terminologies that are external to the filtering system 106. These standard terminologies are sometimes referred to herein as external standard terminologies. For example, data relating to diagnostic and clinical data may be encoded using the Systematized Nomenclature of Medicine—Clinical Terms (SNOMED CT) standard; data describing laboratory test results may be encoded using the Logical Observation Identifiers Names and Codes (LOINC) standard; and prescription drug data may be encoded using the RxNorm standard. Clinical data also may be encoded utilizing one or more of the International Statistical Classification of Diseases and Related Health Problems (such as ICD-9 or ICD-10) standards.

Although the exemplary embodiment illustrates the health-related information as being stored in the electronic health records on the electronic storage device 130, other embodiments are possible. For example, the health care providers 102 could provide the health-related information 138 directly to each other.

The intelligent filtering system 106 provides the capability to sort through a vast amount of health-related information 138, such as from the patient's health related information stored in the data storage device 130 or received from other healthcare providers 102, to identify relevant information. An example of the intelligent filtering system 106 is illustrated and described in more detail with reference to FIGS. 2-12.

Although the intelligent filtering system 106 is illustrated as a system separate from the healthcare providers 102 computing devices 120, 122, 124, and 126 and from the health information exchange system 104, in other embodiments the intelligent filtering system 106 is or operates as a part of one or more of these systems. In some embodiments, the intelligent filtering system 106 is a part of an electronic medical records system in which the caregiver interacts to generate patient notes to document a patient encounter and to review the patient's historical record.

Figure 2:
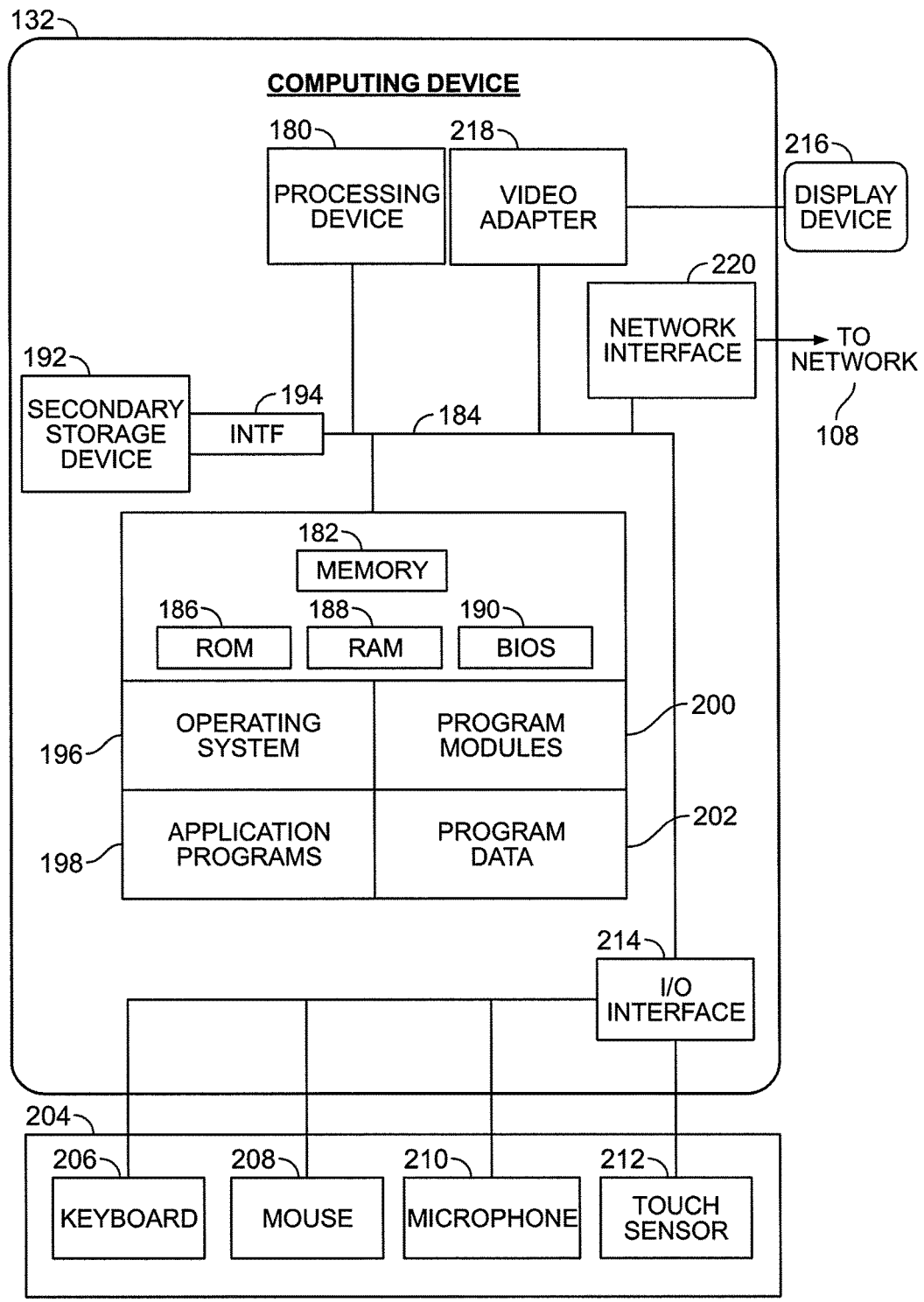
FIG. 2 illustrates an exemplary architecture of a computing device that can be used to implement aspects of the present disclosure.

FIG. 2 illustrates an exemplary architecture of a computing device that can be used to implement aspects of the present disclosure, including any of the plurality of healthcare provider 102 computing devices 120, 122, 124, and 126, the health information exchange computing device 128, and the intelligent filtering computing device 132. More specifically, the computing device illustrated in FIG. 2 can be used to execute the operating system, application programs, and software modules (including the software engines) described herein. By way of example, the computing device will be described below as the intelligent filtering system 106 computing device 132. To avoid undue repetition, this description of the computing device will not be separately repeated herein for each of the other computing devices, including computing devices 120, 122, 124, 126, and 128, but such devices can also be configured as illustrated and described with reference to FIG. 2.

The computing device 132 includes, in some embodiments, at least one processing device 180, such as a central processing unit (CPU). A variety of processing devices are available from a variety of manufacturers, for example, Intel or Advanced Micro Devices. In this example, the computing device 132 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 132 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 132, such as during start up, is typically stored in the read only memory 186.

The computing device 132 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media store nonvolatile storage of computer readable instructions (including application programs and program modules), data structures, and other data for use or communication by the computing device 132.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media.

Figure 4:
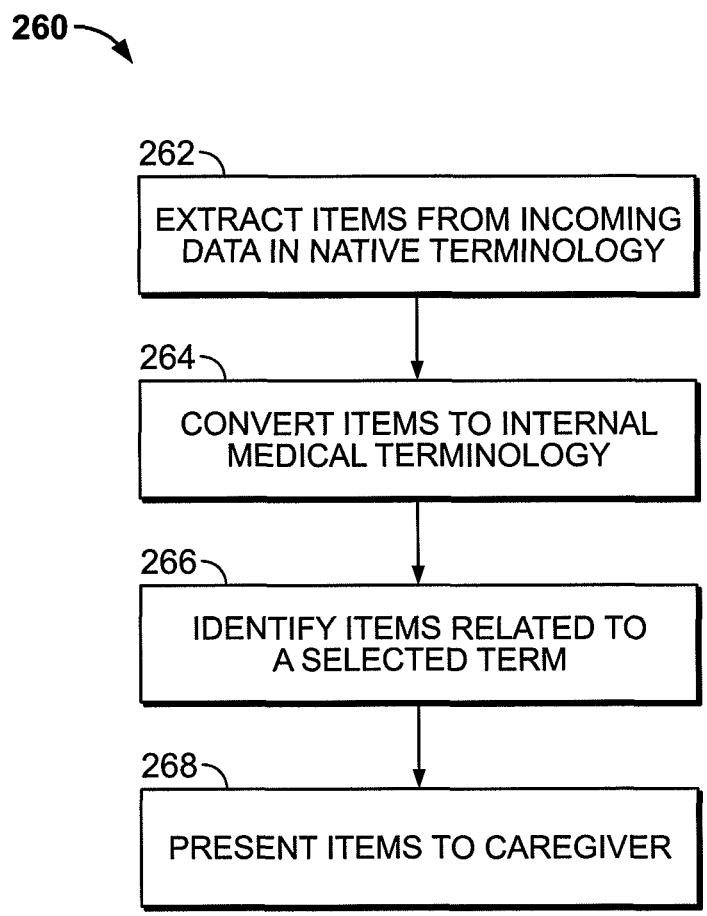
FIG. 4 is a flow chart illustrating an example method of filtering medical data.

A number of program modules can be stored in secondary storage device 192 or memory 182, including an operating system 196, one or more application programs 198, other program modules 200 (such as the engines 230, 232, 234, and 236 described herein with reference to FIG. 4), and program data 202. The computing device 132 can utilize any suitable operating system, such as Microsoft Windows™, Google Chrome™, Apple OS, and any other operating system suitable for a computing device. Other examples can include Microsoft, Google, or Apple operating systems, or any other suitable operating system used in tablet computing devices.

In some embodiments, a user provides inputs to the computing device 132 through one or more input devices 204. Examples of input devices 204 include a keyboard 206, mouse 208, microphone 210, and touch sensor 212 (such as a touchpad or touch sensitive display). Other embodiments include other input devices 204 such as a digital pen. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the input/output interface 214 is possible as well, and includes infrared, BLUETOOTH® wireless technology, 802.11a/b/g/n, cellular, or other radio frequency communication systems in some possible embodiments.

In this example embodiment, a display device 216, such as a monitor, liquid crystal display device, projector, or touch sensitive display device, is also connected to the system bus 184 via an interface, such as a video adapter 218. In addition to the display device 216, the computing device 132 can include various other peripheral devices (not shown), such as speakers or a printer.

When used in a local area networking environment or a wide area networking environment (such as the Internet), the computing device 132 is typically connected to the network 108 through a network interface 220, such as an Ethernet interface. Other possible embodiments use other communication devices. For example, some embodiments of the computing device 132 include a modem for communicating across the network 108.

The computing device 132 typically includes at least some form of computer readable media. Computer readable media includes any available media that can be accessed by the computing device 132. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 132.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 2 is also an example of programmable electronics, which may include one or more such computing devices, and when multiple computing devices are included, such computing devices can be coupled together with a suitable data communication network so as to collectively perform the various functions, methods, or operations disclosed herein.

Figure 3:
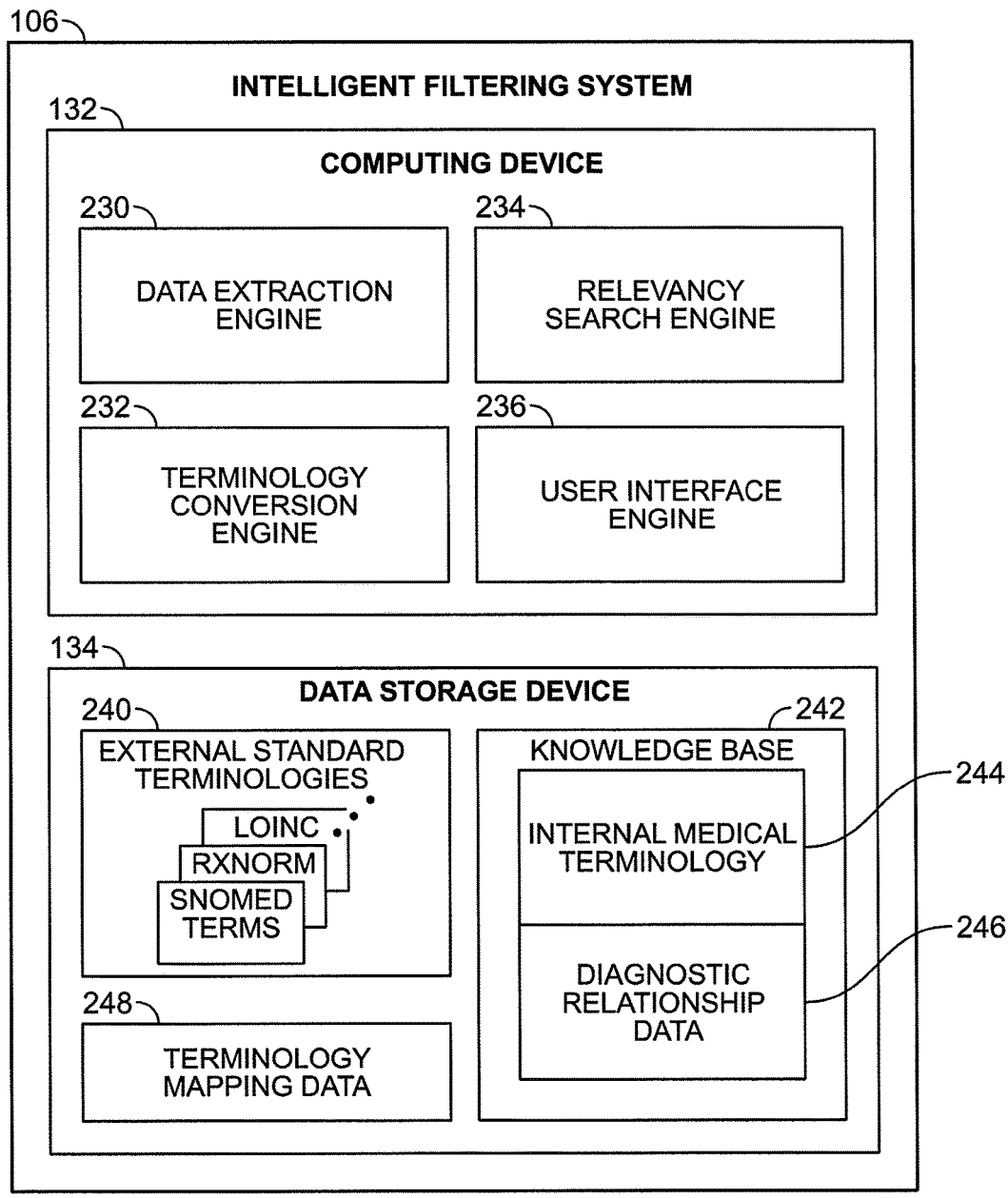
FIG. 3 is a schematic block diagram illustrating an example of an intelligent filtering system.

FIG. 3 is a schematic block diagram illustrating an example of the intelligent filtering system 106, shown in FIG. 1. The intelligent filtering system includes a computing device 132 and a data storage device 134.

The data storage device 134 can be a part of the computing device 132 (such as memory 182 or secondary storage device 192, shown in FIG. 2), or can be a separate data storage device. For example, the data storage device 134 can be a separate database, which can itself include one or more computing devices, in some embodiments. In any event, the data storage device 134 includes one or more computer readable storage devices that store digital data. Examples of computer readable storage devices are described herein.

The computing device 132 includes one or more engines that are executed by the computing device to perform particular functions. In this example, the computing device 132 includes a data extraction engine 230, a terminology conversion engine 232, a relevancy search engine 234, and a user interface engine 236. A brief exemplary description of each engine 232, 234, 236, and 238 is provided below, while a more detailed explanation and additional examples are provided herein.

The data extraction engine 230 receives incoming health-related information 138, extracts items from the information, and saves it in a common format.

The terminology conversion engine 232 converts the items from the health-related information 138 from the native terminologies into an internal medical terminology 244. The internal medical terminology is terminology used internal to the intelligent filtering system as opposed to terminology that received from sources external to the intelligent filtering system such as ICD codes.

The relevancy search engine 234 searches through the converted health-related information to identify those items that are related to a particular term or otherwise relevant to a particular situation.

The user interface engine 236 presents the relevant items from the health-related information 138 to the caregiver, while selectively choosing not to present certain information to the caregiver that is determined to be irrelevant to the present item. Presenting the relevant items to the caregiver can include displaying the items on a display device 216 of the computing device 132, or sending the relevant items across the network 108 for display on another computing device (e.g., computing devices 120, 122, 124, or 126). In another possible embodiment, the items are stored on a computing device or sent to another computing device without displaying the items to the caregiver. For example, the items can be used for subsequent processing.

The data storage device 134 includes, for example, external standard terminologies definitions 240; a knowledge base 242 including an internal medical terminology definition 244 and diagnostic relationship data 246; and terminology mapping data 248.

The external standard terminologies definitions 240 includes data that describes the multiple different external standard terminologies that may be used to encode health-related information 138 that is received by the intelligent filtering system. Examples of external standard terminologies include SNOMED-CT, LOINC, RxNorm, ICD-9, and ICD-10. Other standard terminology definitions can also be included.

As one example, the external standard terminology definitions can include a separate table for each standard terminology. Within each table, the standard terms are listed along with the corresponding codes that are used to represent the standard terms. The data used to populate the external standard terminology definitions 240 is obtained from the respective organization that manages each standard.

The knowledge base 242 contains data that is used by the intelligent filtering system for, at least, internal processing of the data, as described herein. The knowledge base includes an internal medical terminology 244 and diagnostic relationship data 246.

The internal medical terminology 244 is a single terminology that is used by the intelligent filtering system 106. In other words, incoming data is converted into the internal medical terminology 244 so that all data uses a common terminology. An example of a suitable internal medical terminology 244 is the MEDCIN standard medical terminology developed by Medicomp Systems, Inc. of Chantilly, Va. The MEDCIN standard medical terminology includes approximately 280,000 terms. Each of the terms is associated with an internal medical terminology code that uniquely identifies each term.

In addition to the internal medical terminology 244, the knowledge base 242 also includes diagnostic relationship data 246. The diagnostic relationship data 246 defines relationships between the terms of the internal medical terminology 244. For example, the internal medical term for "asthma" is linked to other terms that are diagnostically related to asthma, such as "difficulty breathing," "cough," and "wheezing." In this example, each of the related terms are common findings that are associated with a diagnosis of asthma in a patient. In some embodiments the diagnostic relationship data 246 includes a separate table for each diagnosis included in the internal medical terminology 244. For example, the diagnosis of asthma has a table which includes a list of all terms within the internal medical terminology 244 that have a relationship to the diagnosis of asthma. An example of such a table is illustrated in FIG. 9.

Terminology mapping data 248 defines the relationships between the items in the external standard terminologies definitions 240 and the internal medical terminology 244. As one example, each term of the internal medical terminology 244 has a table that includes a list of each of the corresponding terms in the external standard terminologies definitions 240. This permits the computing device 132 to convert between the external standard terminologies 240 and the internal medical terminology 244 utilizing the terminology conversion engine 232.

The engines 230, 232, 234, and 236 utilize the data stored in the data storage device in order to perform the operations of the intelligent filtering system 106, as illustrated in FIG. 4.

FIG. 4 is a flow chart illustrating exemplary operations performed by the intelligent filtering system 106. FIG. 4 also illustrates an exemplary method 260 of filtering health-related information. In this example, the method 260 includes one or more operations 262, 264, 266, and 268.

The method 260 begins when health-related information 138 is received from an external source, such as from a healthcare provider 102, from the health information exchange system 104 (both shown in FIG. 1). Examples of the health-related information 138 includes the encounter note 140, prescription refill 142, encounter note 144, and discharge summary 146, shown in FIG. 1. In alternative embodiments, the health-related information 138 can be received from sources other than the health information exchange. For example, the health-related information could be receive directly from the healthcare provider 102 for processing, extracted from patient health records hosted by or stored at the intelligent filtering system itself, or from some other source.

Once the health-related information 138 has been received, the operation 262 extracts items from incoming data in the native terminology. In some embodiments the operation 262 is performed by the data extraction engine 230, shown in FIG. 3.

As previously discussed, the health-related information 138 can be encoded utilizing one or more of a variety of external standard terminologies. In addition to the use of different terminologies, the health-related information 138 is also provided in various different formats. The operation 262 removes the differences in formatting by extracting the items from the health-related information 138 and storing the items in a common format. The operation 262 utilizes the external standard terminology definitions 240 (FIG. 3) to identify the items within the health-related information 138. An example of operation 262 is illustrated and described in more detail herein with reference to FIG. 5.

After items have been extracted from the health-related information 138, the items are then converted in operation 264 into the internal medical terminology. In some embodiments, the operation 264 is performed by the terminology conversion engine 232, shown in FIG. 3.

The conversion between the native terminologies in which the health-related information 138 is received and the internal medical terminology 244, is performed utilizing the terminology mapping data 248 (shown in FIG. 3). Examples of operation 264 are illustrated and described in more detail with reference to FIGS. 6-8.

After the items have been converted into the internal medical terminology 244, operation 266 is performed to identify the items in the health-related information 138 that are related to a selected term. The selected term is, in some embodiments, the clinical problem that the caregiver is currently evaluating for the patient. In some embodiments, the operation 266 is performed by the relevancy search engine 234.

In some embodiments, operation 266 begins by receiving from a caregiver one or more selected terms. For example, the user interface engine 236 (FIG. 3) is used to prompt the caregiver to select one or more diagnoses that are being considered or for which the patient is being evaluated. Terms related to things other than a diagnosis also can be selected by the caregiver, such as a particular finding (e.g., "cough").

In another possible embodiment, the term is pre-selected by the computing device. For example, if the intelligent filtering system 106 is being used by the cardiologist 114 (FIG. 1), the intelligent filtering system 106 may automatically select one or more cardiology terms. As another example, the term may be selected based on the patient's stated purpose for the visit, such as "chest pain." In another possible embodiment, the term is automatically selected by the computing device based on predetermined criteria.

Once the one or more terms are selected, a search is performed through the converted health-related information (which is encoded in the internal medical terminology 244), to identify any items that are related to the selected term or terms.

Figure 10:
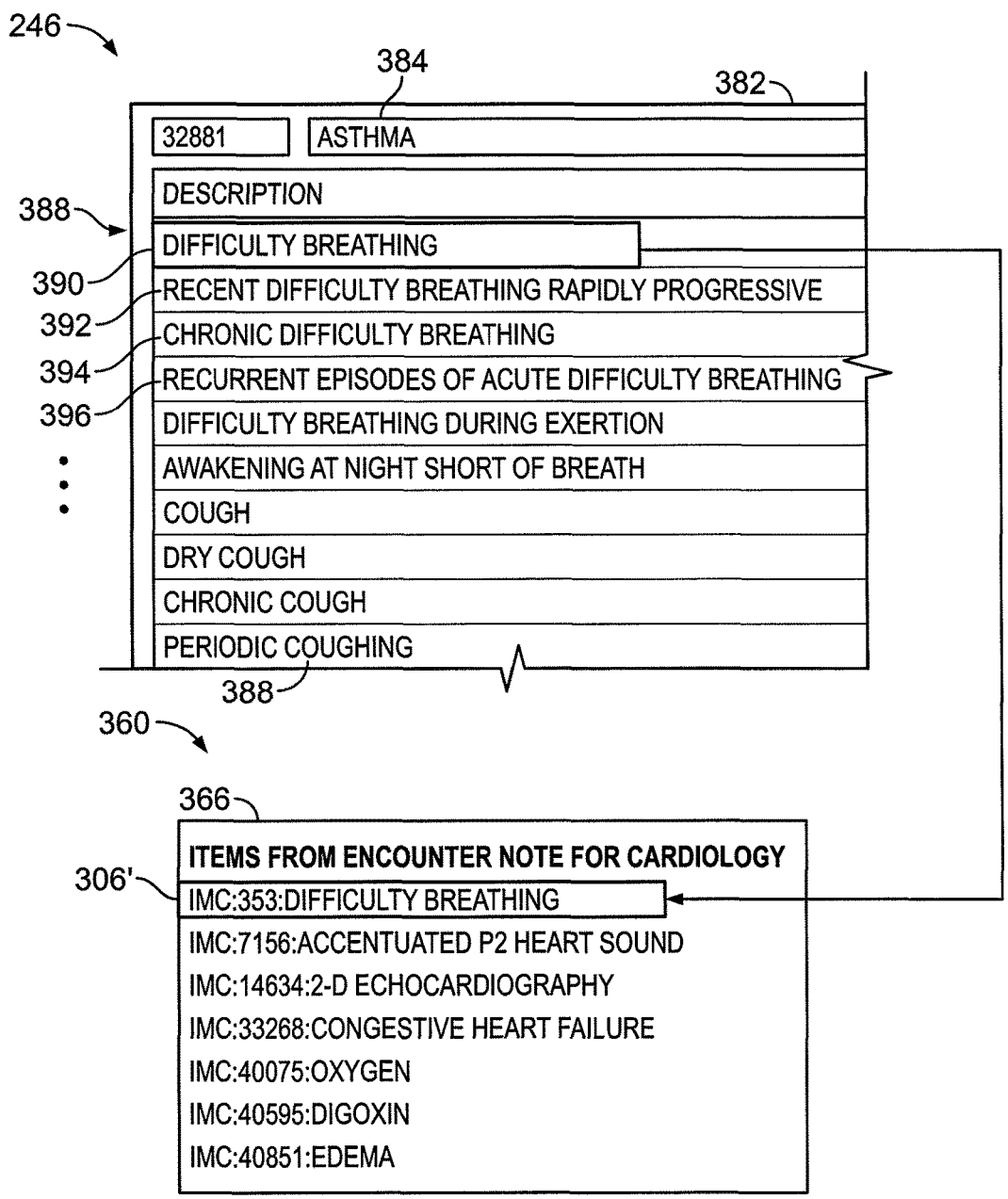
FIG. 10 is a schematic diagram further illustrating the identification of items from the health-related information.

In some embodiments, operation 266 utilizes the knowledge base 242 to identify such items. For example, if the search term is "asthma," the diagnostic relationship data 246 is used to identify the set of terms in the internal medical terminology 244 that are related to asthma. The relevancy search engine 234 obtains the set of terms, and then conducts a search across the health-related information 138 to determine whether any of those terms can be found. The relevant portions of the health-related information 138, which include at least items containing terms related to the selected term, are then stored for subsequent use. An example is illustrated in FIG. 9-10.

Once the relevant items of the health-related information 138 have been identified, operation 268 is performed in some embodiments to present the items identified within the health-related information 138 to the caregiver. In some embodiments, operation 268 is performed by the user interface engine 236.

Figure 11:
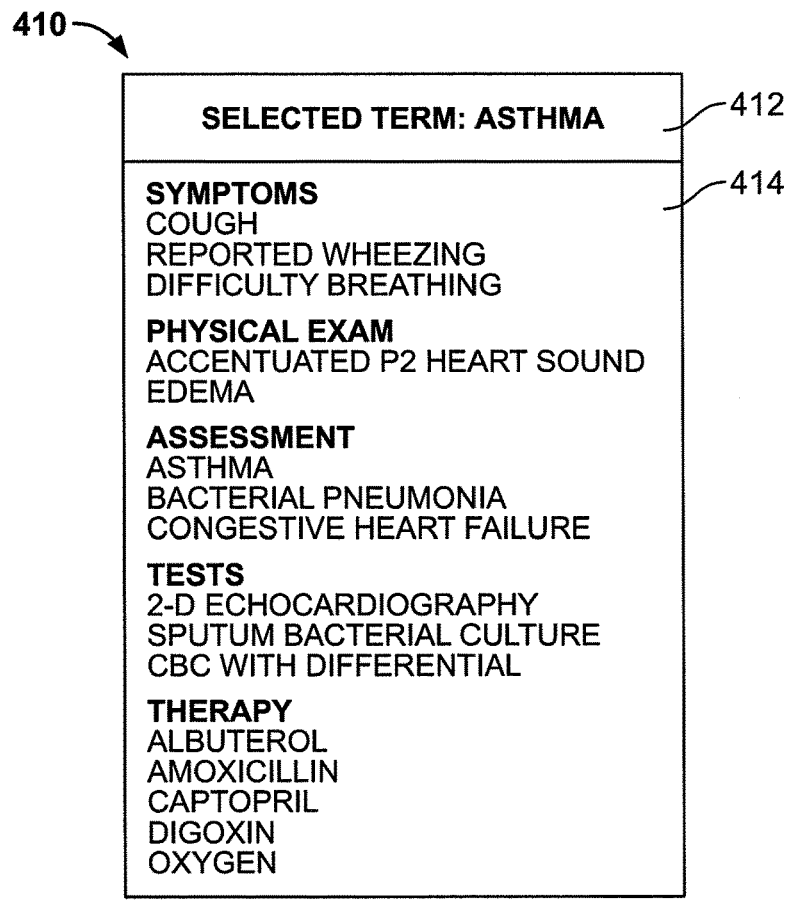
FIG. 11 is a screen shot of an example user interface display showing the items in the health-related information that relate to the selected term.
Figure 12:
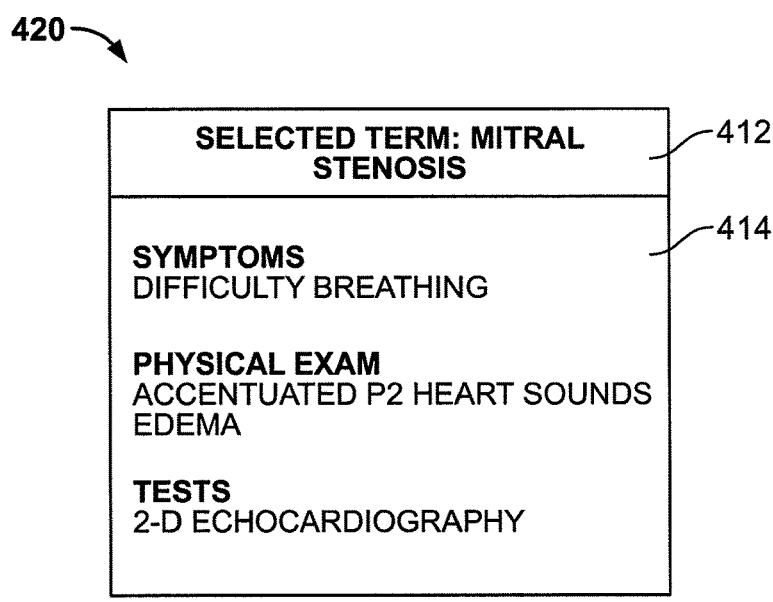
FIG. 12 is a screen shot of another example user interface display showing the items in the health-related information that relate to another selected term.

As an example, the caregiver is presented with a user interface display that shows the items from the health-related information 138 that are relevant to asthma. In this way the caregiver is able to quickly review the relevant portions of the patient's medical record without having to search through a large volume of information that is irrelevant to the present encounter with the patient. Examples of displays generated by the user interface engine 236 and during operation 268 are shown in FIGS. 11-12.

Figure 5:
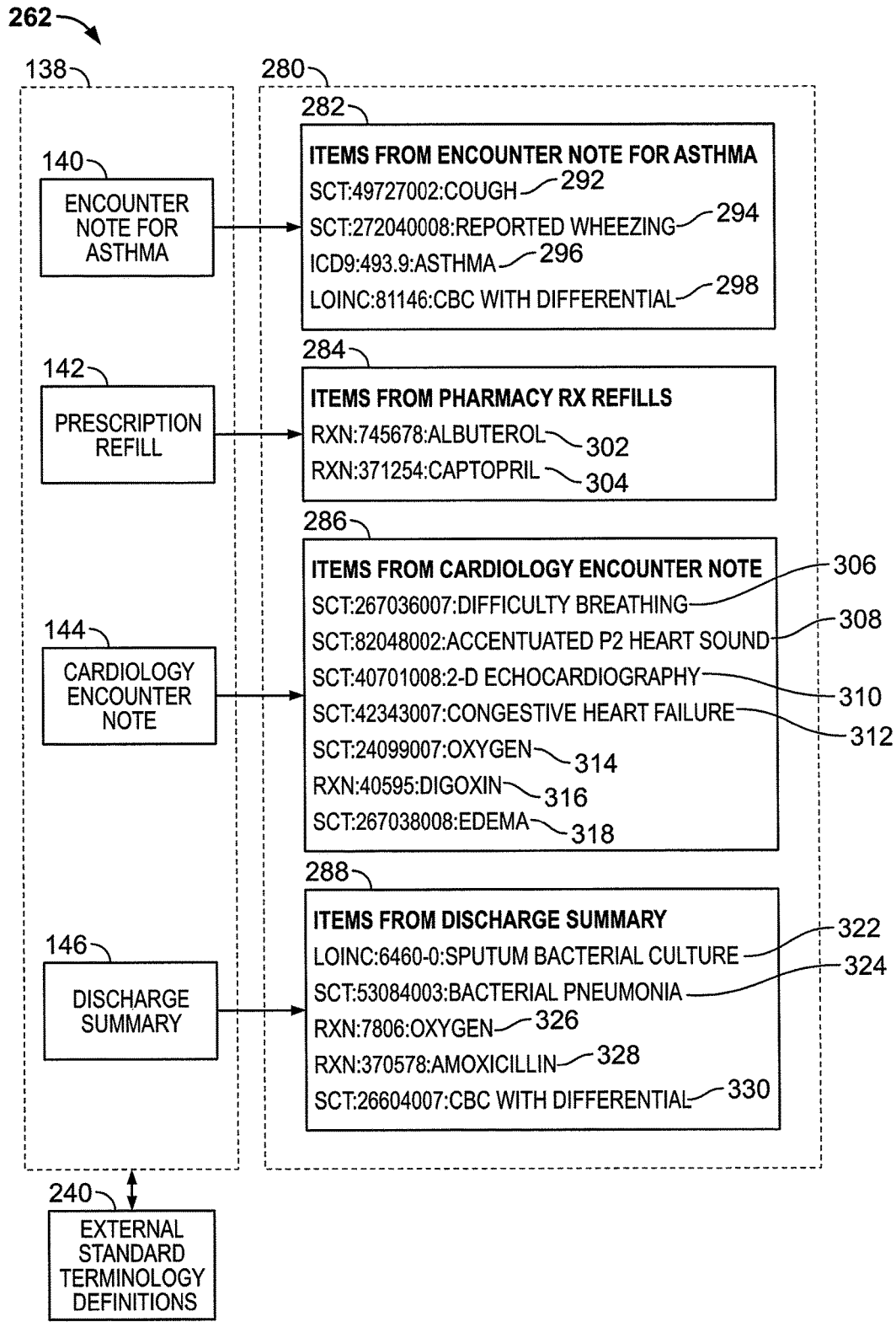
FIG. 5 is a schematic diagram illustrating the extraction of items from incoming health-related information.

FIG. 5 is a schematic diagram illustrating an example of operation 262, shown in FIG. 4, such as performed by the data extraction engine 230, shown in FIG. 3. In this example, the operation 262 involves the use of the external standard terminology definitions 240 to extract items from the health-related information 138 and to generate the health-related information 280.

As shown in the example of FIG. 1, the health-related information 138 includes data from a variety of sources, including an encounter note 140 from the primary care provider 110, a prescription refill 142 from the pharmacy 112, an encounter note from a cardiologist 114, and a discharge summary 146 from the hospital 116.

The health-related information 138 can be in a variety of different formats. As a result, it is desirable to extract the items from the health-related information 138 and save the items in a common format as health-related information 280. In this example, the items from the encounter note 140 are extracted and saved in a list 282. Similarly, the items from the prescription refill 142, the encounter note 144, and the discharge summary 146 are extracted and saved in lists 284, 286, and 288.

To generate the lists, the external standard terminology definitions 240 can be used to identify items within the health-related information that corresponds to a term from one of the external standard terminologies. A scan of the health-related information is performed, and if an item is found that matches a term in one of the external standard terminologies, that item is added to the respective list 282, 284, 286, or 288 of health-related information 280.

In the example, the encounter note 140 was scanned and four items were identified, including items 292, 294, 296, and 298. Items 292 and 294 were identified as terms in the SNOMED-CT standard terminology, while item 296 was identified as a term in the ICD-9 standard terminology, and term 298 was identified as a term of the LOINC terminology. For each term, the list 282 includes an identifier of the standard terminology in which the term was found, a code for the term, and a description of the term. Some embodiments include additional information, such as values or other information retrieved from the health-related information 138. In yet other embodiments, the list 282 includes only the codes, or a combination of the codes and any other desired information.

The lists 284, 286, and 288 are similarly generated, such that the list 284 includes items 302 and 304, the list 286 includes items 306, 308, 310, 312, 314, 316, and 318, and the list 288 includes items 322, 324, 326, 328, and 330.

FIG. 6 is a schematic diagram illustrating an example of operation 264, shown in FIG. 4, such as performed by the terminology conversion engine 232, shown in FIG. 3, in some embodiments. In this example, the operation 264 involves the use of the terminology mapping data 248, such as a terminology mapping table 340 associated with asthma, to convert the items from the health-related information 138 (e.g., the list 282) into the internal medical terminology.

In this example, the items in the list 282 are to be converted into the internal medical terminology, as defined by the internal medical terminology definition 244 (FIG. 3). More specifically, this example illustrates the conversion of the item 296.

Item 296 is an ICD-9 code for asthma, having the code 493.9. To convert this code into the internal medical terminology, the terminology conversion engine retrieves the terminology mapping data for the ICD-9 external standard terminology, and conducts a search within that terminology for the code "493.9."

The search finds a matching cell 342 of the terminology mapping table 340.

The terminology conversion engine then determines the term of the internal medical terminology that is associated with the terminology mapping table 340. In this case, the term is asthma, which has the internal code of 328881. This code is then saved in computer readable storage medium as the conversion of the item 296.

Figure 7:
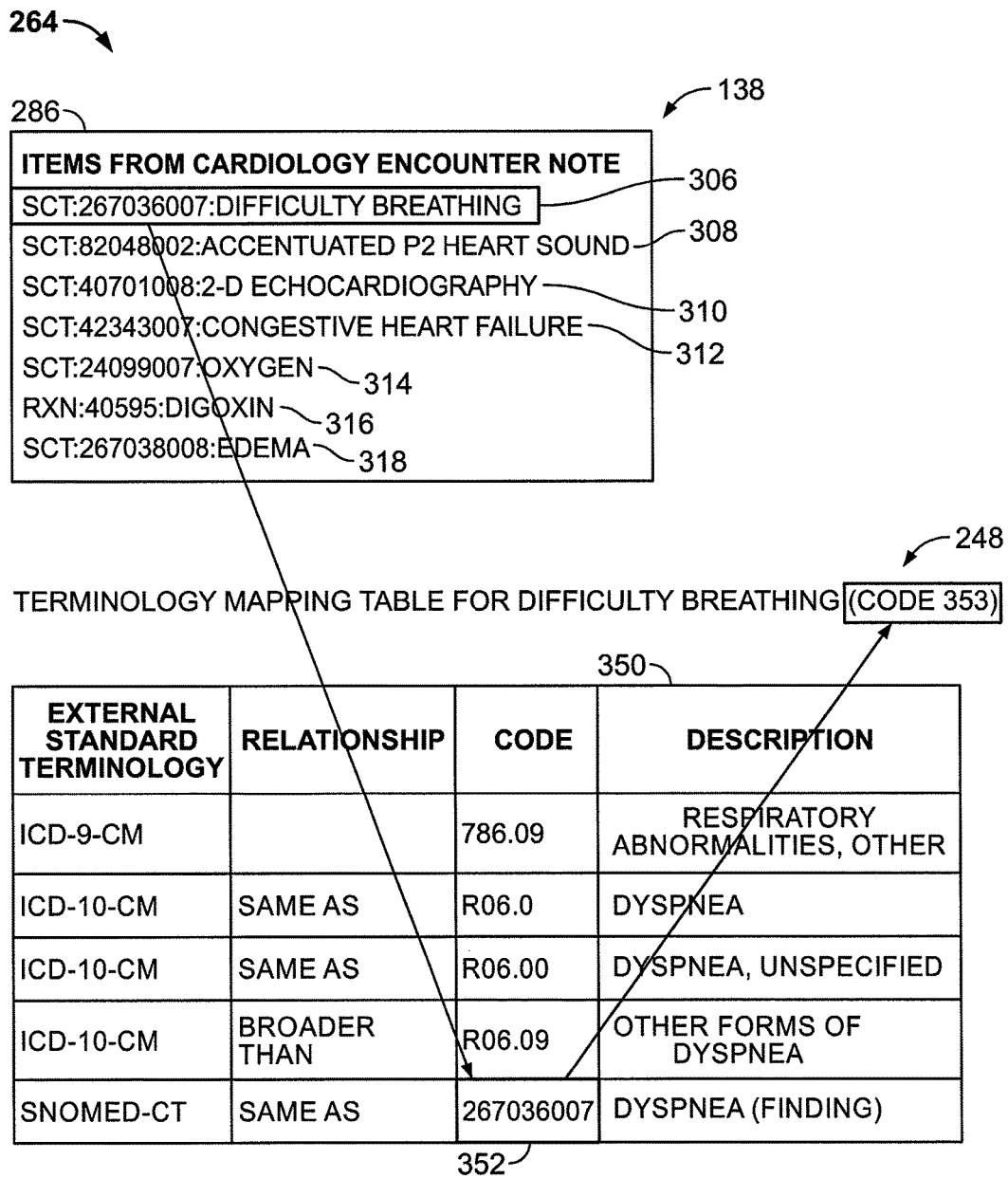
FIG. 7 is a schematic diagram illustrating another example of the conversion of health-related information to an internal medical terminology.

The process continues for each item in the health-related information 138. FIG. 7 illustrates another example.

FIG. 7 is a schematic diagram illustrating another example of the conversion of health-related information items into an internal medical terminology. The conversion utilizes the terminology mapping data 248.

In this example, an item 306 from the list 286 is to be converted into the internal medical terminology. Item 306 was determined to contain a SNOMED-CT code associated with difficulty breathing, having the code 267036007.

To convert this item into the internal medical terminology, the terminology conversion engine 232 conducts a search within the terminology mapping data 248 associated with the SNOMED-CT standard terminology, to identify a term having the code 267036007. The search results in a match in cell 352 of table 350.

The terminology conversion engine 282 then determines the term of the internal medical terminology that is associated with the table 350. In this case, the term is difficulty breathing, having an internal medical code 353. Accordingly, the internal medical code 353 is stored as the conversion of item 306 into the internal medical terminology.

The process is repeated for items 308, 310, 312, 314, 318, and any other items to be evaluated from the health-related information 138, such as those in lists 284 and 288 (FIG. 5). The result is illustrated in FIG. 8.

FIG. 8 is a schematic diagram illustrating the health-related information 360 after conversion to the internal medical terminology. The health-related information 360 includes lists 362, 364, 366, and 368.

List 362 is a list of items 292, 294, 296, and 298 (FIG. 5) after conversion into the internal medical terminology. For example, item 296' now includes the internal medical code (IMC) 328881 for asthma, as shown in FIG. 6.

Lists 364, 366, and 368 were similarly converted. For example, item 306' now includes the internal medical code 353 for difficulty breathing.

FIG. 9 is a schematic diagram illustrating an example of operation 266, shown in FIG. 4, such as performed by the relevancy search engine 234, shown in FIG. 3, in some embodiments. In this example, the operation 266 is performed for a selected term of asthma, to identify items within the health-related information 360 (FIG. 8) relating to asthma.

The operation 266 involves the use of the diagnostic relationship data 246, which defines the relationships between the terms in the internal medical terminology 244. In some embodiments, the diagnostic relationship data 246 includes tables including a table 382.

Once a selected term has been identified, the relevancy search engine 234 retrieves the table 382 from the diagnostic relationship data 246 associated with the selected term. For example, the table 382 associated with asthma (internal medical code 32881) is retrieved, as shown by label 384.

Table 382 includes a list of 281 terms 388 (see count 386) that are related to the asthma term in the diagnostic relationship data 246. The intelligent prompting column 387 identifies how strong the relationship is between the selected term (asthma) and the other listed terms 388. An intelligent prompting value of 1 indicates that the listed term is one of the hallmark findings associated with asthma. An intelligent prompting value of 2 indicates a more detailed finding associated with asthma. A term that has no value listed in the intelligent prompting column is a term that a physician would not typically think of as a primary indicator for asthma, but is still considered to have some correlation (or even an inverse correlation) to asthma.

The listed terms 388 include term 390 for difficulty breathing, term 392 for recent difficulty breathing rapidly progression, term 394 for chronic difficulty breathing, a term 396 for recurrent episodes of acute difficulty breathing, etc.

In some embodiments, table 382 includes the internal medical code for each term. For example, table 382 could include the internal medical code 353 for difficulty breathing. In yet another embodiment, the description of the term is replaced by the internal medical code.

The relevancy search engine 234 then utilizes the terms 388 to conduct a search of the health-related information 360 to find items in the health-related information 360 that match one of the listed terms 388, and are therefore associated with asthma. An example is shown in FIG. 10.

FIG. 10 is a schematic diagram further illustrating a portion of operation 266, shown in FIG. 4. The operation 266 utilizes the diagnostic relationship data 246, including a table 382, to search within the health-related information 360 for items associated with a selected term, such as asthma.

After identifying the table 382 associated with the selected term, the health-related information 360 (shown in FIG. 8) is searched to determine if any of the listed terms 388 within the table 382 can be found.

In this example, the listed term 390 for difficulty breathing, is first considered. A search is conducted of the items in the health-related information 360, and a matching item 306' in list 366 is found. Accordingly, the relevancy search engine 234 (FIG. 3) determines that item 306' in the health-related information 360 is related to the selected term of asthma.

The process is then continued for each of the listed terms 388 in the table 382, until all items within the health-related information 360 that are related to asthma are identified. The results are shown in FIG. 11.

FIG. 11 is a screen shot of an example user interface display 410 providing the results of the intelligent filtering performed by the intelligent filtering system 106. In some embodiments, the display 410 is generated by the user interface engine 236, for example.

User interface display 410 includes a selected term display 412 and a results display 414. The selected term display 412 indicates that a search was conducted for the selected term. The results display 414 identifies all (or a subset) of the items within the health-related information 360 that are related to the selected term.

In this example, the selected term was asthma. Upon completion of the search for items relating to asthma, the results are generated and displayed in the results display 414. The results include a list of 16 items that were located in the health-related information 360 that are related to the selected term (shown in selected term display 412) of asthma. In addition, the items in the results display 414 are sorted in some embodiments to permit the caregiver to more quickly review the results. In this example, the categories include symptoms, physical exam, assessment, tests, and therapy. The appropriate category is determined from the internal medical terminology 244, which assigns one of these categories to each of the terms in the terminology.

The user interface display 410 permits the caregiver to view a subset of the health-related information that is relevant to the selected term, rather than requiring the caregiver to look through all of the health-related information 138, such as shown in FIG. 5. This display 410 provides only that information that is needed by the caregiver, and does not display items that are determined to have no relevance to the selected term.

If duplicate items are found in the health-related information 360, the user interface display 410 can remove such duplicates, if desired. For example, results display 414 includes only a single item for CBC with differential, even though the item was listed in both the encounter note for asthma (list 362 in FIG. 8) and the discharge summary (list 368 also in FIG. 8).

In some embodiments, each item in the results display 414 is associated with a date. The date is assigned to the item according to the date of the health-related information from which it was retrieved. For example, the cough item was retrieved from the encounter note for asthma (list 362 in FIG. 8), and is therefore assigned the date of that encounter. The date can be used for a variety of purposes. For example, the date can be displayed in the result display 414 for each item. As another example, the date can be used to display the results in a table format, where each column in the table represents a date of an encounter or other health-related event, and the rows include a list of internal medical terms that are present in the health-related information. A plus symbol represents a positive finding on that date, while a minus symbol represents a negative finding on that date.

In some embodiments terms are associated with an expiration period in the knowledge base 242. If the date associated with an item in the health-related information was so long ago that the expiration period has now passed, the health-related information is not included in the result display 414, in some embodiments.

FIG. 12 illustrates another example user interface display 420 including the results of another search conducted across the health-related information. The user interface display 420 includes selected term display 412 and results display 414.

The previous example illustrated a search involving a search term that was already present in the patient's medical record. In other words, the health-related information 138 (FIG. 1) already included an encounter note 140 for asthma (which contained the item 296 for Asthma, shown in FIG. 5), and so it is not surprising that the patient's medical record contained items associated with asthma.

This example illustrates a search conducted for a term that is not present in the patient's health-related information. More specifically, mitral stenosis is chosen as the selected term in selected term display 412.

Operation 266 (FIG. 4) is then performed utilizing this selected term. For example, the table associated with mitral stenosis is retrieved from the diagnostic relationship data 246, in the same way that table 382 was retrieved for asthma. The listed terms 388 are then identified, and a search is conducted of the health-related information 360 (FIG. 8) for any of the listed items.

The results of the search are displayed in results display 414. The results include four items, including difficulty breathing, accentuated p2 heart sounds, edema, and 2-d electrocardiography.

This illustrates how important information within the health-related information 138 can be quickly identified by a caregiver utilizing the intelligent filtering system 106, even if the patient has never been evaluated for the condition identified by a selected term.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A method of filtering health-related information in at least one of a plurality of computing devices in a health information exchange network, the method comprising:

at a respective computing device in the health information exchange network:
receiving electronic health-related information over the network, the electronic health-related information consisting of items encoded in one or more external standard terminologies;
generating at least one list of health-related terms provided in the received electronic health-related information;
converting each list of health-related terms from the received electronic health-related information and encoded in the one or more external standard terminologies to equivalent terms in an internal medical terminology, which is stored in a data structure in memory;
receiving a selected search term for comparison with the converted terms in the received electronic health-related information, wherein each converted term is associated with a strength of relationship value which indicates the strength of relationship between the converted term and the selected term, and wherein the strength of relationship value indicating the strength of relationship is stored in a separate table created upon conversion of the received electronic health-related information to equivalent terms in the internal medical terminology;
identifying, by accessing the separate table, at least one term in the converted list of health-related terms that is diagnostically related to the selected search term, wherein the at least one converted term is determined to be diagnostically related to the selected search term based on the strength of relationship value in comparison with a predetermined value threshold;
verifying a direct correlation link between the selected term and any converted term in the list of health-related terms having a strength of relationship above the predetermined value threshold;
establishing an indirect correlation link between the selected search term and any converted term in the list of health-related terms having a strength of relationship below the predetermined value threshold; and
displaying, on a user interface, the selected search term and each converted term in the list of health-related terms having a direct or indirect correlation link to the selected term.

2. The method of claim 1, wherein the external standard terminologies are selected from the group consisting of: the Systematized Nomenclature of Medicine—Clinical Terms (SNOMED CT) standard, the Logical Observation Identifiers Names and Codes (LOINC) standard, the RxNorm standard, and the International Statistical Classification of Diseases and Related Health Problems (ICD-9 and ICD-10) standards.

3. The method of claim 1, wherein the quantity of terms in the converted list of health-related terms having a direct or indirect correlation link to the selected term is less than the quantity of items in the converted health-related information.

4. The method of claim 1, wherein generating converted electronic health-related information includes searching for a term of an external standard terminology in a terminology mapping table and identifying an item encoded in the internal medical terminology that is associated with the term of the external standard terminology.

5. The method of claim 1, comprising:
prompting the caregiver through the user interface to identify a clinical problem which is to be evaluated, and wherein the clinical problem is the selected term.

6. The method of claim 5, comprising:
prompting the caregiver through the user interface to identify a second clinical problem which is to be evaluated and receiving a selection of a second selected term.

7. The method of claim 6, wherein the selected term is a first selected term, the method comprising:
identifying one or more terms in the internal medical terminology related to one or more of the first selected term and the second selected term.

8. The method of relevant claim 1, wherein generating a user interface comprises displaying only the at least one first and second identified items from the converted health-related information directly and indirectly linked to the selected diagnosis.

9. The method of claim 1, wherein the selected term is determined based on predetermined criteria that includes a purpose for a patient's visit.

10. The method of claim 1, wherein the selected term is determined based on predetermined criteria that include a specialty of a caregiver.

11. The method of claim 1, comprising:
sending each converted term in the list of health-related terms having a direct or indirect correlation link to the selected term to another computing device on the health information exchange network.

12. The method of claim 1, comprising:
displaying each converted term in the list of health-related terms having a direct or indirect correlation link to the selected term based on relevancy to one of plural medical categories and in an order of relevancy to the selected term.

13. The method of claim 1, wherein an entry in the list of health-related terms links to a table of additional terms and the indirect correlation link is established via any determined relationship between a respective converted term and the selected search term in a higher level table in the list of health-related terms.

14. An intelligent filtering system comprising:
at least one computing device including at least one processing device; and
at least one computer readable storage device having data instructions recorded thereon, which when executed by the computing device cause the at least one computing device to generate:
a data extraction engine that extracts health-related items from electronic health-related information received over the computing network in a native terminology;
a terminology conversion engine that generates converted health-related information by converting the health-related items received in the native terminology internal medical terminology;
a relevancy search engine that establishes links between the converted health-related information and a selected diagnosis, wherein establishing the links includes identifying at least one first item in the converted health-related information that is directly correlated to the selected diagnosis and identifying at least one second item in the converted health-related information that is indirectly correlated to the selected diagnosis, wherein a direct correlation link is verified between a term in the converted health-related information having a strength of relationship value with the selected diagnosis that is above a predetermined value threshold, and wherein an indirect correlation link is established for a term in the converted health-related information having a strength of relationship value with the selected diagnosis that is below the predetermined value threshold; and
a user interface engine that presents to a caregiver the selected diagnosis and the at least one first and second items in the converted health-related information directly and indirectly linked to the selected diagnosis.

15. The intelligent filtering system of claim 14, wherein the user interface engine presents the converted health-related items that are related to the selected diagnosis as part of a patient note, and wherein the patient note is used by the caregiver to document the patient encounter.

16. The intelligent filtering system of claim 14, wherein the user interface engine is configured to display the at least one first and second items of the converted electronic health-related information based on relevancy to one of plural medical events and in an order of relevancy to the selected diagnosis in accordance with a current medical encounter of the patient.

17. The intelligent filtering system of claim 14, wherein the converted health-related information is a table that includes a link to another table of additional terms and the indirect correlation link is established via any determined relationship between a respective converted term and the selected search term in a higher level table in the converted health related information.

18. An intelligent filtering computing device, comprising:
an interface connected to a health information exchange network;
memory for storing at least an internal medical terminology; and
a processor configured to:
receive electronic health-related information generated in a native medical terminology;
extract health-related terms from the received electronic health-related information;
convert the health-related terms from the native medical terminology into the internal medical terminology to generate converted electronic health-related information;
identify items within the converted electronic health-related information that are related to a selected term through direct and indirect links between the converted electronic health-related information and the selected term, wherein a direct correlation link is verified for a term in the converted electronic health-related information having a strength of relationship value above a predetermined value threshold, and wherein an indirect correlation link is established for a term in the converted electronic health-related information having a strength of relationship value below the predetermined value threshold; and
control a display for displaying at least the selected term and the converted electronic health-related information directly and indirectly linked to the selected term.

19. The intelligent filtering computing device of claim 18, wherein the identified items in the converted health-related information related to the selected term are displayed according to relevancy to one of plural medical categories and in an order of relevancy to the selected term in association with the first medical encounter.

20. The intelligent filtering computing device of claim 18, wherein the converted electronic health-related information is a table that includes a link to another table of additional terms and the indirect correlation link is established via any determined relationship between a respective converted term and the selected term in a higher level table in the converted electronic health-related information.

* * * * *